United States Patent
Mertens

(10) Patent No.: US 9,789,477 B2
(45) Date of Patent: Oct. 17, 2017

(54) SYNTHESIS OF CRYSTALLINE MOLECULAR SIEVES HAVING THE EUO FRAMEWORK TYPE

(71) Applicant: ExxonMobil Chemical Patents Inc., Baytown, TX (US)

(72) Inventor: Machteld M. W. Mertens, Flemington, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 330 days.

(21) Appl. No.: 14/399,094

(22) PCT Filed: Jun. 7, 2013

(86) PCT No.: PCT/EP2013/061840
§ 371 (c)(1),
(2) Date: Nov. 5, 2014

(87) PCT Pub. No.: WO2013/189766
PCT Pub. Date: Dec. 27, 2013

(65) Prior Publication Data
US 2015/0119620 A1  Apr. 30, 2015

(30) Foreign Application Priority Data
Jun. 18, 2012  (EP) .................................... 12172378

(51) Int. Cl.
*C01B 39/48* (2006.01)
*B01J 29/70* (2006.01)
(Continued)

(52) U.S. Cl.
CPC ....... *B01J 29/7023* (2013.01); *B01J 29/7246* (2013.01); *B01J 29/7446* (2013.01);
(Continued)

(58) Field of Classification Search
CPC ..... B01J 29/7023; B01J 35/023; C01B 39/48; C01B 39/46; C01P 2004/52; C01P 2004/61; C01P 2004/03; C01P 2004/60
See application file for complete search history.

(56) References Cited

U.S. PATENT DOCUMENTS 4,537,754 A * 8/1985 Casci .................. B01J 29/7023
423/326
4,640,829 A   2/1987 Rubin
(Continued)

FOREIGN PATENT DOCUMENTS

EP  0042226  8/1984
EP  0051318  4/1985
(Continued)

OTHER PUBLICATIONS

Millini et al, "Synthesis and characterization of borosilcates with the EUO framework topology", Microporous and Mesoporous Materails, 46, (2001), 191-201.*
(Continued)

*Primary Examiner* — David M Brunsman
(74) *Attorney, Agent, or Firm* — Darryl M. Tyus

(57) ABSTRACT

In a process for the synthesis of a crystalline molecular sieve material having the EUO framework type, a synthesis mixture is provided suitable for the formation of an EUO framework type molecular sieve and comprising N,N,N,N', N',N'-hexamethylhexanediammonium, Q, cations and a colloidal suspension of seed crystals of an EUO framework type molecular sieve. The synthesis mixture is crystallized and an EUO framework type molecular sieve in the form individual crystals and/or aggregates of crystals having an average size, $d_{50}$, as measured by laser scattering, of less than 15 μm is recovered from the synthesis mixture.

12 Claims, 10 Drawing Sheets

(51) Int. Cl.
*B01J 29/72* (2006.01)
*B01J 29/74* (2006.01)
*B01J 29/78* (2006.01)
*B01J 35/00* (2006.01)
*B01J 35/02* (2006.01)
*C07C 5/22* (2006.01)
*C07C 6/12* (2006.01)
*C10G 35/095* (2006.01)
*C10G 45/12* (2006.01)
*C10G 45/64* (2006.01)
*C10G 45/68* (2006.01)
*C10G 47/16* (2006.01)
*C10G 50/00* (2006.01)
*C10G 3/00* (2006.01)
*C10G 11/05* (2006.01)
*C01B 39/46* (2006.01)
*C07C 4/02* (2006.01)

(52) U.S. Cl.
CPC ....... *B01J 29/7846* (2013.01); *B01J 35/0013* (2013.01); *B01J 35/023* (2013.01); *C01B 39/46* (2013.01); *C01B 39/48* (2013.01); *C07C 4/02* (2013.01); *C07C 5/22* (2013.01); *C07C 6/123* (2013.01); *C07C 6/126* (2013.01); *C10G 3/49* (2013.01); *C10G 11/05* (2013.01); *C10G 35/095* (2013.01); *C10G 45/12* (2013.01); *C10G 45/64* (2013.01); *C10G 45/68* (2013.01); *C10G 47/16* (2013.01); *C10G 50/00* (2013.01); *B01J 2229/18* (2013.01); *C01P 2002/72* (2013.01); *C01P 2004/03* (2013.01); *C01P 2004/52* (2013.01); *C01P 2004/60* (2013.01); *C01P 2004/61* (2013.01); *C07C 2521/04* (2013.01); *C07C 2521/06* (2013.01); *C07C 2521/08* (2013.01); *C07C 2521/10* (2013.01); *C07C 2521/16* (2013.01); *C07C 2529/70* (2013.01); *Y02P 30/20* (2015.11)

(56) References Cited

U.S. PATENT DOCUMENTS

| 4,695,667 | A  | * | 9/1987  | Sumitani ............ B01J 29/7023 585/481 |
| 6,337,063 | B1 | * | 1/2002  | Rouleau ............. B01J 20/18 423/705 |
| 6,342,200 | B1 | * | 1/2002  | Rouleau ............. B01J 20/18 423/708 |
| 6,514,479 | B1 | * | 2/2003  | Merlen ............. B01J 29/7023 423/705 |
| 7,264,789 | B1 |   | 9/2007  | Verduijn et al. |
| 7,431,913 | B2 | * | 10/2008 | Caullet ............. B01J 20/18 423/700 |
| 8,557,220 | B2 | * | 10/2013 | Goergen ............. B01J 29/7023 423/700 |

FOREIGN PATENT DOCUMENTS

| FR | 2785201    | 5/2000  |
| FR | 2785278    | 5/2000  |
| WO | 93/08124   | 4/1993  |
| WO | 2006/134249 | 12/2006 |

OTHER PUBLICATIONS

Dodwell et al, "Crystallization of EU-1 and EU-2 in alkali and alkali-free systems", ZEOLITES, (1985), vol. 5, 153-157.*

"Atlas of Zeolite Framework Types", eds. Ch. Baerlocher, L.B. McCusker, D.H. Oson, Elsevier, Sixth Revised Edition, (2007).

Casci , J. L. et al., "*The Synthesis and Characterisation of Zeolite EU-1*", Proceedings of the International Zeolite Conference, Jan. 1, 1984, pp. 894-904.

Qinghu, Xu et al, "*Synthesis of high-silica EU-1 zeolite in the presence of hexamethonium ions: A seeded approach for inhibiting ZSM-48*", Journal of Colloid and Interface Science, Academic Press, New York, NY, US, vol. 358, No. 1, Mar. 9, 2011, pp. 252-260.

Lee, S. et al., "*Reinvestigation into the synthesis of zeolites using diquaternary alkylammonium ions $(CH_3)_3 N^+(CH_2)_n N^+(CH_3)_3$, with n=3-10 as structure-directing agents*", in Microporous and Mesoporous Materials, vol. 68, pp. 97-104 (2004).

Moini, A. et al., "*Pentamethyl diethylene triamine and its quaternary cations as directing agents in zeolite synthesis: Monitoring the stability of directing agents under hydrothermal conditions*", Zeolites, Elsevier Science Publishing, US, vol. 18, No. 1, Jan. 1, 1997, pp. 2-6.

Shin, J. et al, "*N,N,N,N',N',N'-hexamethylpentanediammonium-MWW layered precursor: A reaction intermediate in the synthesis of zeolites TNU-9 and EU-1*", Microporous and Mesoporous Materials, Elsevier Science Publishing, New York, US, vol. 124, No. 1-3, Aug. 1, 2009, pp. 227-231.

* cited by examiner

SYNTHESIS OF CRYSTALLINE MOLECULAR SIEVES HAVING THE EUO FRAMEWORK TYPE

CROSS REFERENCE TO RELATED APPLICATIONS

This application is a 371 National Stage Application of International Application PCT/EP2013/061840, filed Jun. 7, 2013, and claims the benefit of and priority to European Patent Application No. 12172378.7, filed Jun. 18, 2012, the disclosures of which are hereby incorporated by reference herein in their entireties.

FIELD

This invention relates to methods for the preparation of molecular sieves having the EUO framework type.

BACKGROUND

Molecular sieve materials, both natural and synthetic, have been demonstrated in the past to be useful as adsorbents and to have catalytic properties for various types of hydrocarbon conversion reactions. Certain molecular sieves, such as zeolites, AlPOs, and mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as rigid three-dimensional framework of $SiO_4$ and Periodic Table Group 13 element oxide (e.g., $AlO_4$). The tetrahedra are cross-linked by the sharing of oxygen atoms with the electrovalence of the tetrahedra containing the Group 13 element (e.g., aluminum) being balanced by the inclusion in the crystal of a cation, for example a proton, an alkali metal or an alkaline earth metal cation. This can be expressed wherein the ratio of the Group 13 element (e.g., aluminum) to the number of various cations, such as $H^+$, $Ca^{2+}/2$, $Sr^{2+}/2$, $Na^+$, $K^+$, or $Li^+$, is equal to unity.

Molecular sieves that find application in catalysis include any of the naturally occurring or synthetic crystalline molecular sieves. Examples of these molecular sieves include large pore zeolites, intermediate pore size zeolites, and small pore zeolites. These zeolites and their isotypes are described in "Atlas of Zeolite Framework Types", eds. Ch. Baerlocher, L. B. McCusker, D. H. Olson, Elsevier, Sixth Revised Edition, 2007, which is hereby incorporated by reference. A large pore zeolite generally has a pore size of at least about 7 Angstroms, an intermediate pore size zeolite generally has a pore size from about 5 Angstroms to less than about 7 Angstroms and includes, and a small pore size zeolite has a pore size from about 3 Angstroms to less than about 5.0 Angstroms.

Intermediate pore size zeolites include those having the EUO framework type. Referring to the above-mentioned Atlas of Zeolite Framework Types, EUO framework type zeolites have a uni-dimensional microporous crystalline framework, with channels having diameters of 4.1×5.4 Angstroms, with large side pockets. According to N. A. Briscoe et al., Zeolites 8, 74-76 (1988), the lateral pockets have a depth of 8.1 Angstroms and a diameter of 6.8×5.8 Angstroms.

Molecular sieves with the EUO framework type include EU-1, TPZ-3 and ZSM-50. Zeolite EU-1 and zeolite TPZ-3, as well as their preparation from a synthesis mixture comprising a N,N,N,N',N',N'-hexamethyl-1,6-hexamethylene diammonium compound as structure directing agent are described in EP-A-0,042,226 and in EP-A-0,051,318. U.S. Pat. No. 4,640,829 discloses ZSM-50 zeolite and its synthesis in the presence of dibenzyldimethylammonium ions as a structure directing agent.

In an article entitled "Reinvestigation into the synthesis of zeolites using diquaternary alkylammonium ions $(CH_3)_3N^+(CH_2)_nN^+(CH_3)_3$, with n=3-10 as structure-directing agents", in *Microporous and Mesoporous Materials*, 68, 97-104 (2004), Lee et al. report that $Me_6$-diquat-5 cations $[(CH_3)_3N^+(CH_2)_5N^+(CH_3)_3$, also referred to as N,N,N,N',N',N'-hexamethylpentanediammonium] exhibit a wide diversity of phase selectivity by directing the synthesis of EU-1, ZSM-12, ZSM-48, MCM-22 or mordenite depending on the oxide composition of the synthesis mixture.

A later article entitled "N,N,N,N',N',N'-hexamethylpentanediammonium-MWW precursor: A reaction intermediate in the synthesis of zeolites TNU-9 and EU-1", by Shin et al in *Microporous and Mesoporous Materials*, 124, 227-231 (2009) reports that the layered precursor of the zeolite MCM-22, generally referred to as MCM-22(P), is a reaction intermediate in the synthesis of zeolites TNU-9 and EU-1 in the presence of $Me_6$-diquat-5 cations, depending on the $Na^+$ content of the synthesis mixture.

U.S. Pat. No. 6,514,479 discloses EUO framework type zeolite crystals having a size of less than 5 µm, wherein at least a portion of the EUO zeolite crystals is in the form of crystal aggregates with a specific granulometry such that the value of Dv,90 is in the range of 200 µm to 40 µm. According to this document, this means that, when analyzed by laser diffraction granulometry after being subjected to ultrasound, 90% of the aggregates have an equivalent sphere diameter in the range of 200 µm to 40 µm. The crystals are synthesized using alkylated polymethylene α-ω diammonium salts, preferably 1,6-N,N,N,N',N',N'-hexamethylhexamethylenediammonium salts, as structure directing agent and in the presence of seeds of one or more zeolites of the framework type EUO, LTA, LTL, FAU, MOR, MAZ, OFF, FER, ERI, BEA, MFI, MTW, MTT, LEV, TON and NES, IM-5 or a NU-85, NU-86, NU-88 zeolite.

U.S. Pat. No. 7,264,789 discloses a colloidal suspension of a LEV framework type crystalline molecular sieve and its use as seeds in the manufacture of a crystalline molecular sieve selected from the group consisting of the MFS, CHA, OFF, MOR, FER, MAZ, EUO and ERI/OFF, framework types.

U.S. Pat. No. 6,514,479, FR-A-2785201, WO-A1-2006/134249, FR-A-2785278, and the article entitled "The synthesis and characterization of zeolite EU-1", in *Proceedings of the International Zeolite Conference*, 894-904 (1984), disclose the preparation of zeolites having the EUO framework type in the presence of seeds of an EUO framework type zeolite. The use of said seeds has the advantage to reduce the crystallization time of the EUO zeolite and to improve the flexibility in the reaction mixture composition.

According to the present invention it has now been found that, in the synthesis of EUO framework type crystalline molecular sieves, the use of colloidal seeds of previously synthesized EUO framework type material can be used to tailor the particle size and the particle size distribution of the as synthesized EUO framework type molecular sieves. In particular, the addition of increasing amounts of colloidal seeds of previously synthesized EUO framework type material allows the production of substantially single EUO crystals with tailored average size $d_{50}$ values, as measured by laser scattering, decreasing to a minimum generally at around 1 µm or below.

SUMMARY

In one aspect, the invention resides in a process for the synthesis of a crystalline molecular sieve material having the EUO framework type, the process comprising:

(a) providing a synthesis mixture suitable for the formation of an EUO framework type molecular sieve and comprising N,N,N,N',N',N'-hexamethylhexanediammonium, Q, cations and a colloidal suspension of seed crystals of an EUO framework type molecular sieve;

(b) crystallizing said synthesis mixture; and (c) recovering from said synthesis mixture an EUO framework type molecular sieve in the form of individual crystals and/or aggregates of crystals having an average size, $d_{50}$, as measured by laser scattering, less than 15 µm.

In one embodiment, the individual crystals and/or aggregates of crystals have an average size, $d_{50}$, as measured by laser scattering, less than 5 µm and a span $(d_{90}-d_{10}/d_{50})$ of less than 2.0, preferably less than 1.8.

Generally, the synthesis mixture contains at least 0.1 ppm, such as from 0.1 ppm to 2,000 ppm, preferably from 0.1 ppm to 1,000 ppm, more preferably from 1 ppm to 500 ppm, by weight of said colloidal seed crystals of an EUO framework type molecular sieve.

Conveniently, the synthesis mixture further comprises a source of an alkali or alkaline earth metal (M), a source of an oxide of a tetravalent element Y, a source of a trivalent element X, and water, and has a composition, in terms of mole ratios, within the following ranges:

$YO_2/X_2O_3$ at least 30;
$H_2O/YO_2$ about 15 to about 80;
$OH^-/YO_2$ about 0.2 to about 0.8;
$M/YO_2$ about 0.2 to about 0.8; and
$Q/YO_2$ about 0.05 to about 0.5.

In a further aspect, the invention resides in a process for the synthesis of a crystalline molecular sieve material having the EUO framework type by crystallization of a synthesis mixture suitable for the manufacture of that molecular sieve, the process comprising the step of adjusting the amount of colloidal EUO seed crystals present in the synthesis mixture to control the particle size and/or span of the product, wherein said amount is in a range of 0.1 ppm to 2,000 ppm by weight, preferably of 0.1 ppm to 1,000 ppm by weight, more preferably of 1 ppm to 500 ppm by weight, based on the total weight of the synthesis mixture.

In a further aspect, the invention relates to the use of colloidal EUO seed crystals, preferably in the form of a suspension, in the synthesis of a crystalline molecular sieve material having the EUO framework type, said molecular sieve being obtained by crystallization of a synthesis mixture suitable for its manufacture, wherein the amount of colloidal EUO seed crystals present in the synthesis mixture is adjusted to control the particle size and/or span of the EUO product. Said synthesis mixture usually comprises N,N,N,N',N',N'-hexamethylhexanediammonium, Q, cations and the colloidal EUO seeds are most often used in an amount in the range of 0.1 ppm to 2,000 ppm by weight, preferably of 0.1 ppm to 1,000 ppm by weight, more preferably of 1 ppm to 500 ppm by weight, based on the total weight of the synthesis mixture.

In a further aspect, the invention resides in a crystalline molecular sieve material having the EUO framework type produced by the process described herein and use of the molecular sieve in hydrocarbon conversion reactions, particularly cracking, reforming, hydrofining, aromatization, oligomerisation, isomerization, dewaxing, and hydrocracking (e.g., naphtha to light olefins, higher to lower molecular weight hydrocarbons, alkylation, transalkylation, disproportionation or isomerization of aromatics).

In a still further aspect, the invention relates to a crystalline molecular sieve material having the EUO framework type and composed of individual crystals and/or aggregates of crystals having an average size, $d_{50}$, as measured by laser scattering, of less than 15 µm and a span $(d_{90}-d_{10}/d_{50})$ of less than 2.0.

DETAILED DESCRIPTION OF THE EMBODIMENTS

Figure 1:
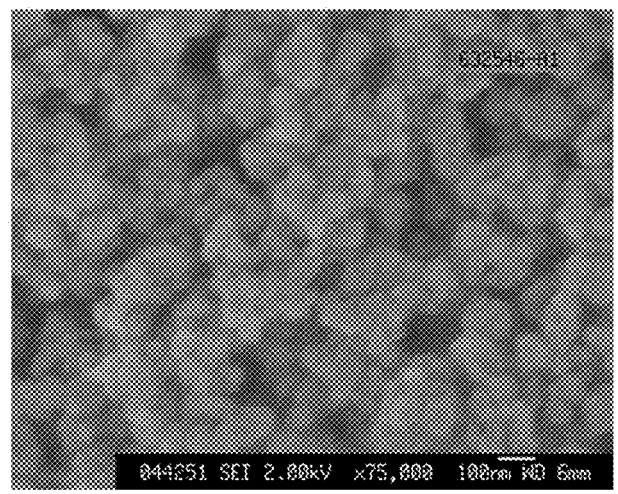
FIG. 1 is an SEM micrograph of crystals produced in accordance with Example 1.

Described herein is a process for the synthesis of EUO framework type crystalline molecular sieves by crystallization of an aqueous synthesis mixture comprising N,N,N,N',N',N'-hexamethylhexanediammonium, Q, cations as the structure directing agent and a colloidal suspension of seed crystals of an EUO framework type molecular sieve. In particular, it is found that, by controlling the amount of colloidal EUO seeds added to the synthesis mixture, the particle size of EUO product can be tuned to small average size $d_{50}$ values, as measured by laser scattering, of less than 15 μm while keeping a particle size distribution within narrow limits, namely with a span $(d_{90}-d_{10}/d_{50})$ of less than 2.0, such as less than 1.8.

In the present invention, the EUO framework type crystalline molecular sieve, or EUO product, is recovered from the synthesis mixture in the form of particles which can be either individual crystals and/or aggregates of crystals. As used herein, the term "aggregate of crystals" means an ensemble formed by at least two individual crystals of zeolite having at least one point between them. Said particles, i.e. said crystals and/or aggregates of crystals forming the EUO product, are characterized by an average size $d_{50}$ and by a span $(d_{90}-d_{10}/d_{50})$ as measured by particle size analysis using laser scattering. The experimental procedure for this measurement is defined in more details below.

As used herein, the expression "colloidal suspension", refers to a suspension containing discrete finely divided particles dispersed in a continuous liquid phase; preferably, it refers to a suspension that is stable, in the sense that no visible separation occurs or sediment forms, in a period sufficient for the use intended, advantageously for at least 10 hours, more advantageously at least 20 hours, preferably at least 100 hours, and more preferably at least 500 hours at ambient temperature (23° C.). The maximum size of the particles for the suspension to remain stable (peptized) will depend to some extent on their shape, and on the nature and pH of the continuous medium, as well as on the period during which the suspension must remain usable. The particles may be spherical, or of other shapes. Where particles are other than spherical, the dimension referred to is their smallest dimension. The colloidal seeds generally have an average diameter of 300 nm or less, in particular of 200 nm or less, more particularly of 100 nm or less, provided that said colloidal seeds form a stable suspension, in the sense that no visible separation occurs or sediment forms, in a period sufficient for the use intended. The colloidal seeds are advantageously incorporated in the synthesis mixture in the form of a suspension, advantageously in an aqueous medium, preferably water, or another liquid component of the synthesis mixture. Less preferably seeds may be added in dry, but not calcined, form. It is believed that calcination significantly reduces the activity of small crystallites to act as seeds; similarly any other treatment that reduces the seeding activity of materials should be avoided.

The synthesis mixture employed in the present process comprises a source of an alkali or alkaline earth metal (M), a source of an oxide of a tetravalent element Y, a source of a trivalent element X, a source of the template cations, Q, and water, typically such that mixture has a composition, in terms of mole ratios, within the following ranges:

$YO_2/X_2O_3$ at least 30;
$H_2O/YO_2$ about 15 to about 80;
$OH^-/YO_2$ about 0.2 to about 0.8;
$M/YO_2$ about 0.2 to about 0.8; and
$Q/YO_2$ about 0.05 to about 0.5.

Suitable sources of the tetravalent element Y depend on the element Y selected but in the preferred embodiments, in which Y is silicon and/or germanium, include colloidal suspensions of silica, fumed silicas, alkali metal silicates, tetraalkyl orthosilicates and germanium oxide. If present, the trivalent element X is normally aluminum and suitable sources of aluminum include hydrated alumina and water-soluble aluminum salts, such as aluminum nitrate. Combined sources of aluminum and silicon may include clays or treated clays such as metakaolin. Other combined sources of X and Y including aluminosilicate zeolites such as zeolite Y may also be used.

Suitable sources of Q are the hydroxides and/or salts of N,N,N,N',N',N'-hexamethylpentanediammonium cations.

The synthesis mixture also contains colloidal EUO seed crystals, which are added to the mixture in an amount from about 0.1 ppm to about 2,000 ppm, preferably from about 0.1 ppm to about 1,000 ppm, such as about 1 ppm to about 500 ppm, with the precise amount depending on the desired crystal size of the EUO product. Thus, in general, the larger the amount of colloidal EUO seed crystals added to the synthesis mixture, the smaller is the crystal size of the EUO product. In particular, by adjusting the colloidal EUO seed addition with the above limits, the EUO product is composed of individual crystals and/or aggregates of crystals having an average size, $d_{50}$, as measured by laser scattering, less than 15 μm, typically less than 5 μm, even down to 1 μm of less. Most often, the EUO product is composed of particles, i.e. individual crystals and/or aggregates of crystals, having an average size $d_{50}$, as measured by laser scattering, of 1 to less than 15 μm, preferably of 1 μm to less than 5 μm, more preferably of 1 to less than 2 μm, for example of 1.0 to 1.5 μm. In addition, the individual crystals and/or aggregates of crystals typically have a span $(d_{90}-d_{10}/d_{50})$ of less than 2.0, normally less than 1.8, in particular 1.6 or less, more particularly 1.5 or less, for instance as low as 1.0 to 1.3 or even as low as 1.0 to 1.2. As used herein, $d_x$ refers to the particle size distribution by volume, obtained by laser scattering, where x is the percentage of the volume of particles having a size smaller than a given value.

The colloidal EUO seeds can be of the same composition as the crystalline molecular sieve material to be synthesized. The colloidal EUO seeds can also be of a different composition such as a different $YO_2/X_2O_3$ ratio than the crystalline molecular sieve material to be synthesized, provided they are of the EUO framework type.

The colloidal EUO seeds, preferably in the form of a colloidal suspension as defined above, can be introduced at any point in the preparation of the EUO framework type crystalline molecular sieve. The colloidal seeds can for instance be introduced before or at the same time as the sources of the metal oxides, or of the organic structuring agent, or of the alkali or alkaline earth metal (M). The colloidal seeds can also be introduced first into the aqueous mixture, or the colloidal seeds can be introduced after introducing the oxide precursors and the structuring agent. In a preferred embodiment, the colloidal seeds are introduced at the same time or after the source of the trivalent element X or at the same time or after the organic structuring agent, or at the same time or after the source of the alkali or alkaline earth metal (M) but before the source of the tetravalent element Y. In a more preferred embodiment, the colloidal seeds are introduced after the source of the trivalent element X, the organic structuring agent, and the source of the alkali or alkaline earth metal (M), but before the source of the tetravalent element Y.

Crystallization of EUO framework type zeolite from the above synthesis mixture can be carried out at either static or stirred conditions in a suitable reactor vessel, such as for example, polypropylene jars or teflon lined or stainless steel autoclaves, at a temperature of about 100° C. to about 200° C., such as about 150° C. to about 200° C. for a time sufficient for crystallization to occur at the temperature used, e.g., from about 1 to about 21 days. The reaction mixture is usually reacted under autogenous pressure, or optionally in the presence of a gas such as nitrogen. Thereafter, the crystals are separated from the liquid, for instance by filtration, decantation or centrifugation, and recovered.

In a further aspect, the invention relates to the use of colloidal EUO seed crystals in the synthesis of a crystalline molecular sieve material having the EUO framework type, said molecular sieve being obtained by crystallization of a synthesis mixture suitable for its manufacture, wherein the amount of colloidal EUO seed crystals present in the synthesis mixture is adjusted to control the particle size and/or span of the EUO product. Said synthesis mixture usually comprises N,N,N,N',N',N'-hexamethylhexanediammonium, Q, cations. In this further aspect, the colloidal EUO seeds are most often used in an amount in the range of 0.1 ppm to 2,000 ppm by weight, preferably of 0.1 ppm to 1,000 ppm by weight, more preferably of 1 ppm to 500 ppm by weight, based on the total weight of the synthesis mixture. In this further aspect, the colloidal EUO seeds are advantageously used in the form of a colloidal suspension.

In a still further aspect, the invention relates to a crystalline molecular sieve material having the EUO framework type and composed of individual crystals and/or aggregates of crystals having an average size, $d_{50}$, as measured by laser scattering, of less than 15 μm and a span $(d_{90}-d_{10}/d_{50})$ of less than 2.0. With particular preference, said crystalline molecular sieve material has an average size, $d_{50}$, as measured by laser scattering, of less than 5 μm, even down to 1 μm or less, in particular of 1 μm to less than 5 μm, more particularly of 1 μm to less than 2 μm, most particularly of 1 μm to 1.5 μm. Said crystalline molecular sieve material also advantageously has a span $(d_{90}-d_{10}/d_{50})$ of less than 1.8, preferably of 1.6 or less, more preferably of 1.5 or less, more particularly of 1.0 to 1.3, for instance of 1.0 to 1.2. In an especially preferred embodiment, said crystalline molecular sieve material is prepared by the process of the present invention in the presence of 50 to 400 ppm by weight of EUO colloidal seeds, for instance in the presence of 75 to 200 ppm by weight of EUO colloidal seeds, based on the total weight of the synthesis mixture.

To the extent desired and depending on the $X_2O_3/YO_2$ molar ratio of the material, any alkali or alkaline earth metal cations in the as-synthesized EUO material can be replaced in accordance with techniques well known in the art by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups 2 to 15 of the Periodic Table of the Elements. As used herein, the numbering scheme for the Periodic Table Groups is as disclosed in Chemical and Engineering News, 63(5), 27 (1985).

The as-synthesized EUO material may also be subjected to treatment to remove part or all of the organic directing agent Q used in its synthesis. This is conveniently effected by thermal treatment in which the as-synthesized material is heated at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. Alternatively, the organic directing agent Q can be removed by treatment with ozone (see, e.g., Parikh et al., Microporous and Mesoporous Materials 76, 17-22 (2004)). The organic-free product, especially in its metal, hydrogen and ammonium forms, is particularly useful in the catalysis of certain organic, e.g., hydrocarbon, conversion reactions. In the present invention, said organic-free molecular sieve in its hydrogen form is referred to as "active form" of the molecular sieve, with or without metal function present, such as Pt or Pd.

The molecular sieve of the present invention may also be intimately combined with a hydrogenating component, such as molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The present molecular sieve, when employed either as an adsorbent or as a catalyst should be dehydrated, at least partially. This can be done by heating to a temperature in the range of 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the EUO material in a vacuum, but a longer time is required to obtain a sufficient amount of dehydration.

The EUO material described herein can be used as an adsorbent or, particularly in its aluminosilicate form, as a catalyst to catalyze a wide variety of organic compound conversion processes including many of present commercial/industrial importance. Examples of suitable conversion processes include, for example, cracking, reforming, hydrofining, aromatization, oligomerisation, isomerization, dewaxing, and hydrocracking (e.g., naphtha to light olefins, higher to lower molecular weight hydrocarbons, alkylation, transalkylation, disproportionation or isomerization of aromatics). Other conversions include the reaction of alcohols with olefins and the conversion of oxygenates to hydrocarbons.

When used as a catalyst, it may be desirable to incorporate the EUO material described herein with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the present EUO zeolite, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the present EUO zeolite include the montmorillonite and kaolin family, which families include the subbentonites, and the kaolins commonly known as Dixie, McNamee, Ga. and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present EUO zeolite also include inorganic oxides, such as silica, zirconia, titania, magnesia, beryllia, alumina, and mixtures thereof.

In addition to the foregoing materials, the present EUO material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of EUO material and inorganic oxide matrix may vary widely, with the EUO content ranging from about 1 to about 90 percent by weight and more usually, particularly when the composite is prepared in the form of beads, in the range of about 2 to about 80 weight percent of the composite.

The invention will now be more particularly described with reference to the Examples and the accompanying drawings.

The SEM micrographs of the Examples were recorded on a JEOL JSM-6340F Field-Emission-Gun scanning electron microscope. Prior to measurement, either a diluted slurry of a washed synthesis mixture or a powder sample (for instance dried one night at 120° C.) is dispersed in water or other liquid such as ethanol, optionally subjected to 5 to 10 minutes ultrasonic treatment, and deposited on SEM holders.

The particle size analysis of the Examples was performed using a Mastersizer APA2000, from Malvern Instruments Limited, equipped with autosampler and a 4 mW laser beam, based on laser scattering by randomly moving particles in a liquid medium. The samples to be measured were recovered from the synthesis mixture and washed with deionized water. The samples were kept in water prior to measurement and sonicated in situ to ensure proper dispersion. The Instrument conditions were as follows: Material Refractive index=1.544, absorption=1, Water Refractive index=1.33; Calculation Model Malvern: General purpose-enhanced sensitivity, In pot mixing time: 50 sec, Sample transfer: auto-concentration, target obscuration: 15%, Pump speed: 2000 RPM, Stirrer speed: 800 RPM, Ultrasonic: continuous 100%, Average of 2 Measurements, Measurement time: 20 sec/20000 snaps, Background time: 20 sec/20000 snaps.

The size distribution of the particles, comprising individual crystals and/or aggregates of crystals, is defined by volume, $dv_x$, referred to as $d_x$ in the present invention, is defined as the equivalent sphere diameter such that x % by volume of the particles have a diameter less than said diameter. In the present invention, these characteristics are obtained directly after zeolite synthesis, which means that no method which can reduce the particle size such as post-synthesis grinding or milling is used before the measurement. The results typically are expressed as $d_{10}$, $d_{50}$, $d_{90}$ and span. A $d_x$ number of, e.g., 1 µm, means that x % of the volume of the particles are smaller than 1 µm. The span is calculated as $[d_{90}-d_{10}/d_{50}]$ and indicates the width of the particle size distribution.

Example 1: Preparation of Colloidal EUO Crystals Using LEV Seeds

Raw Materials:
Alumina source: Aluminum sulphate solution made from $Al_2(SO_4)_3 \cdot 18H_2O$ as supplied by Riedel de Haen (100%).
Silica source: Ultrasil VN 35P-PM as supplied by Degussa (Silica: 92.4%; $Al_2O_3$: 0.11%; $NaO_2$: 0.28%).
Alkali source: NaOH solution made from NaOH pellets as supplied by Sigma-Aldrich (99.9% purity).
Template (R): N,N,N,N',N',N'-hexamethylhexanediammonium bromide as supplied by Sigma-Aldrich (95%+ purity).
Seeding slurry containing 3.5 wt. % of seeds with the LEV structure as prepared according to example 1 of WO 00/06494. The seeds were used as obtained from the synthesis mixture without mechanical size reduction or drying.
Molar composition of synthesis mixture: 0.0167 $Al_2O_3$/ 0.65 NaOH/0.1 Q/$SiO_2$/45 $H_2O$+1000 ppm LEV seeds on total weight of the synthesis mixture.

Synthesis mixture preparation: 1102.6 parts of water were loaded into the synthesis reactor and 118.6 parts of the NaOH solution were added under stirring. Subsequently, 48.43 parts of the alumina solution and 263.8 parts of the template (Q) were added to this mixture which was stirred until homogeneous before the seeds and finally 118.4 parts of the silica source were added. The quantity of seed slurry added was 48.7 parts resulting in 1000 wt. ppm of seed crystals based on the total weight of the synthesis mixture.

Crystallization conditions: The reactor was closed and heated to 160° C. with a heating rate of 20° C./hour while stirring. After 336 hours of crystallization, the reactor was cooled to room temperature; the solid separated from the liquid and washed several times with deionized water. After washing the crystals were re-dispersed in water and stored as such. The concentration of the solids was determined to be 9.06 weight %.

Figure 2:
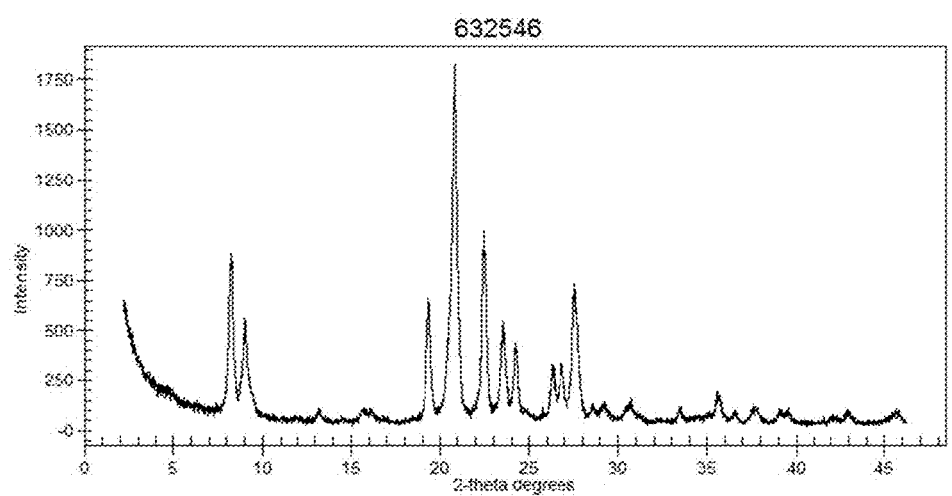
FIG. 2 is an XRD pattern of crystals produced in accordance with Example 1.
Figure 3:
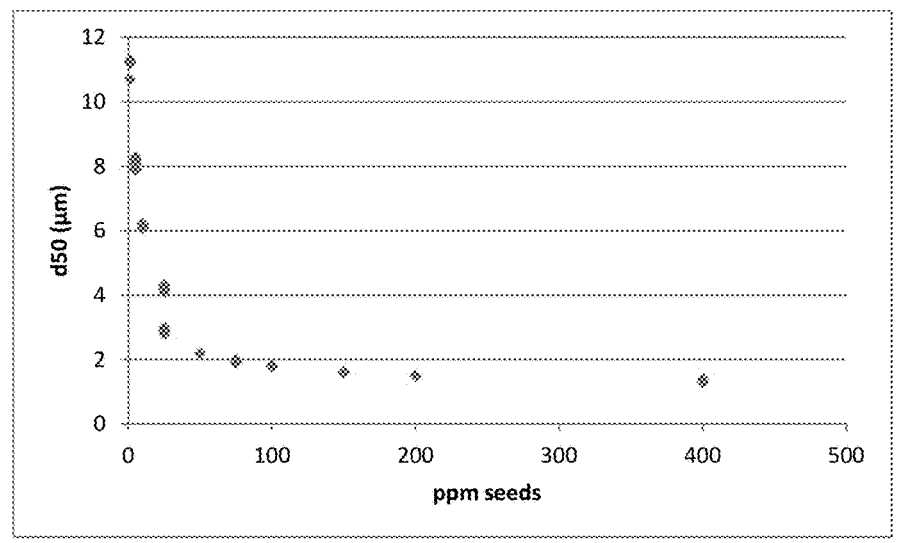
FIG. 3 is a graph of $d_{50}$ (µm) of the crystalline EUO product versus wt ppm EUO seeds in the synthesis mixtures used in Example 2.
Figure 4:
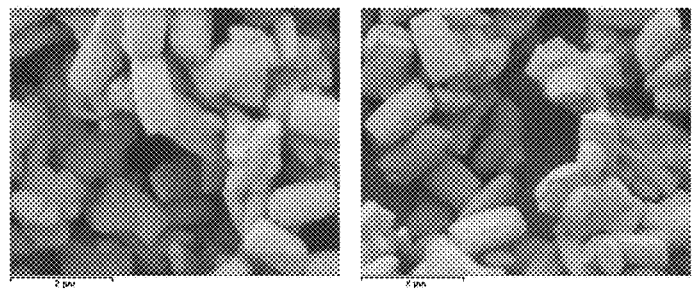
FIG. 4 shows SEM micrographs of two products produced according to Example 2, with 400 wt ppm seeds, and an indicated scale of 2 µm.
Figure 5:
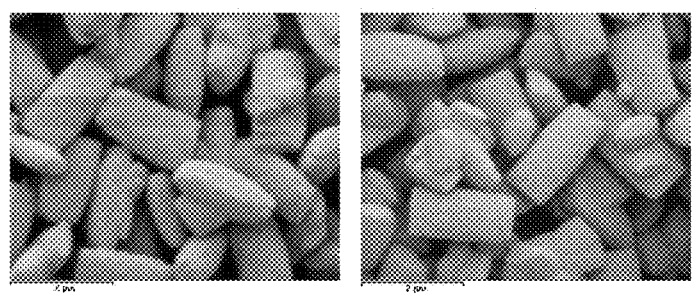
FIG. 5 shows SEM micrographs of two products produced according to Example 2, with 200 wt ppm seeds, and an indicated scale of 2 µm.
Figure 6:
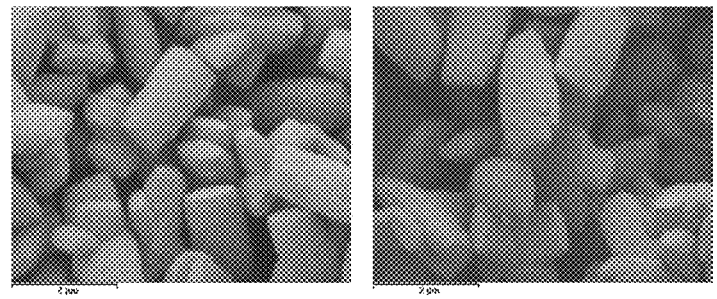
FIG. 6 shows SEM micrographs of two products produced according to Example 2, with 150 wt ppm seeds, and an indicated scale of 2 µm.
Figure 7:
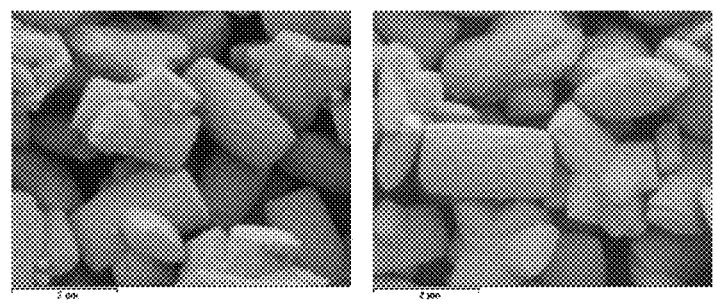
FIG. 7 shows SEM micrographs of two products produced according to Example 2, with 100 wt ppm seeds, and an indicated scale of 2 µm.
Figure 8:
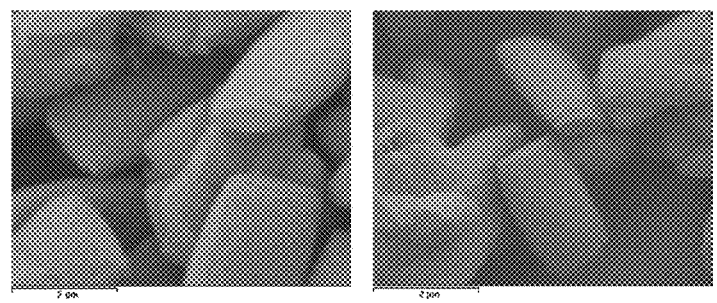
FIG. 8 shows SEM micrographs of two products produced according to Example 2, with 75 wt ppm seeds, and an indicated scale of 2 µm.
Figure 9:
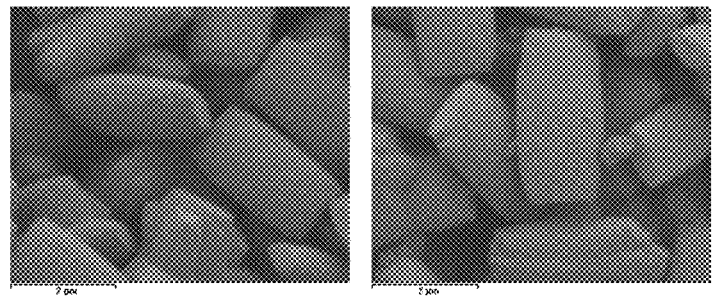
FIG. 9 shows SEM micrographs of two products produced according to Example 2, with 50 wt ppm seeds, and an indicated scale of 2 µm.
Figure 10:
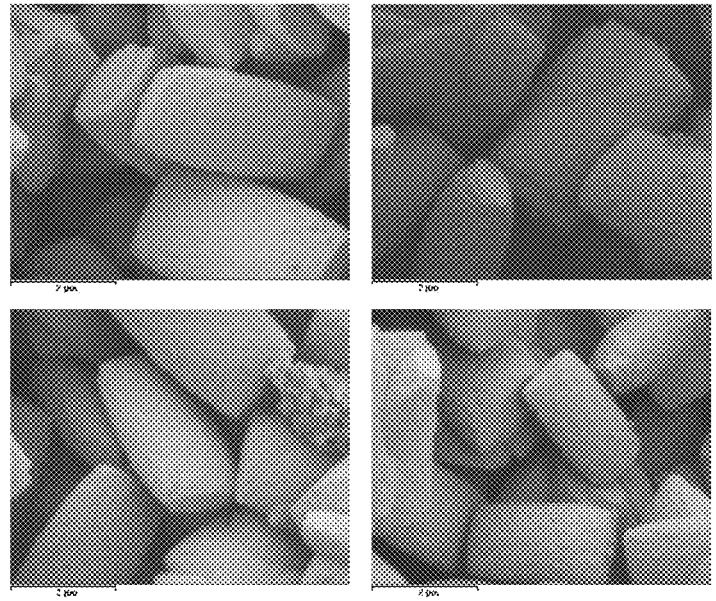
FIG. 10 shows SEM micrographs of four products produced according to Example 2, with 25 wt ppm seeds, and an indicated scale of 2 µm.
Figure 11:
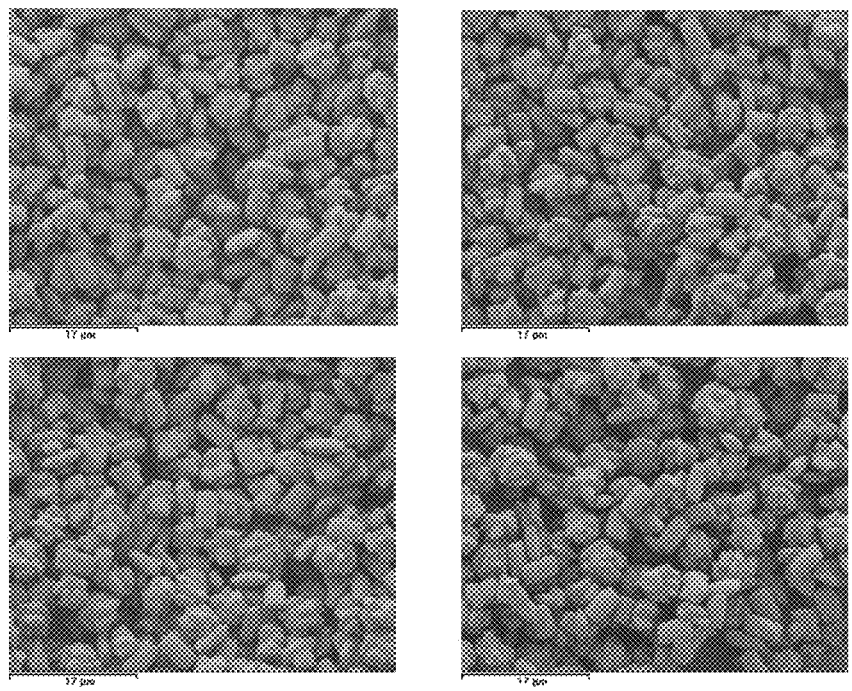
FIG. 11 shows SEM micrographs of four products produced according to Example 2, with 25 wt ppm seeds, and an indicated scale of 17 µm.
Figure 12:
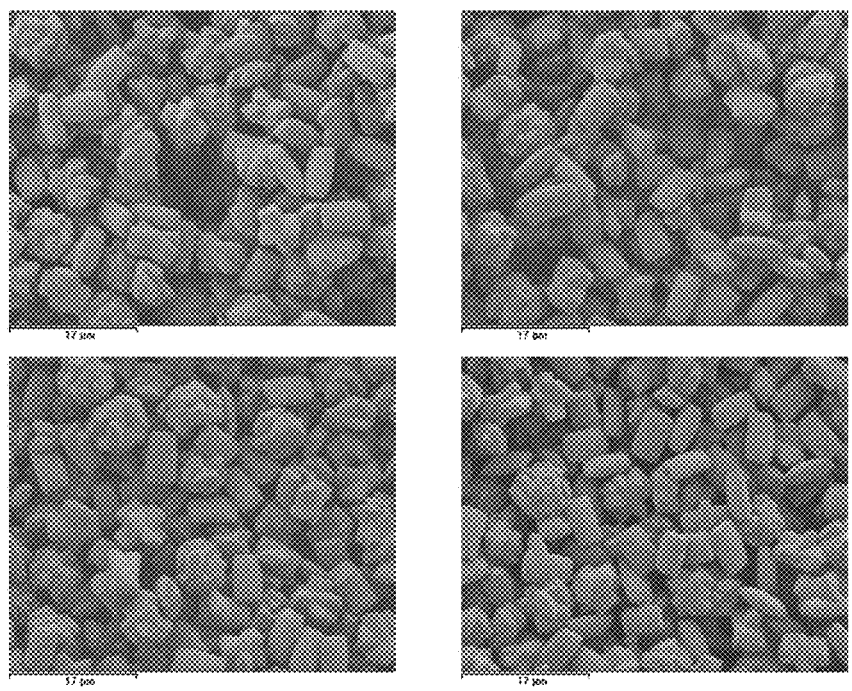
FIG. 12 shows SEM micrographs of four products produced according to Example 2, with 10 wt ppm seeds, and an indicated scale of 17 µm.
Figure 13:
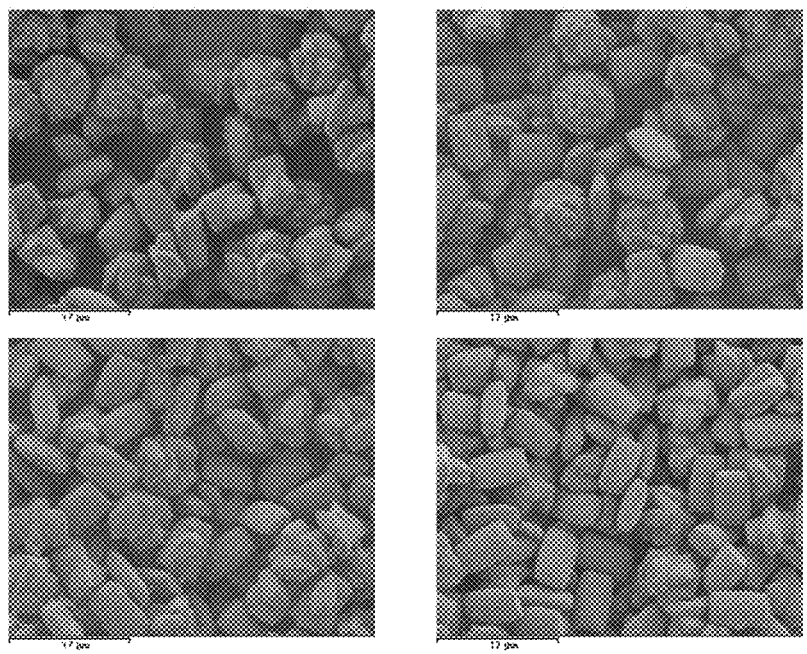
FIG. 13 shows SEM micrographs of four products produced according to Example 2, with 5 wt ppm seeds, and an indicated scale of 17 µm.
Figure 14:
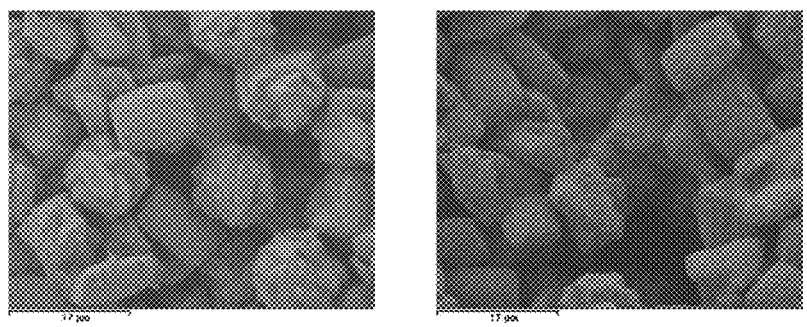
FIG. 14 shows SEM micrographs of two products produced according to Example 2, with 1 wt ppm seeds, and an indicated scale of 17 µm.
Figure 15:
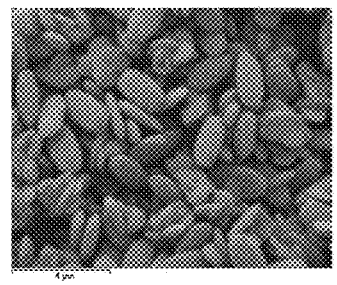
FIG. 15 shows a SEM micrograph of a product produced according to Example 3-1 and an indicated scale of 4 µm.
Figure 16:
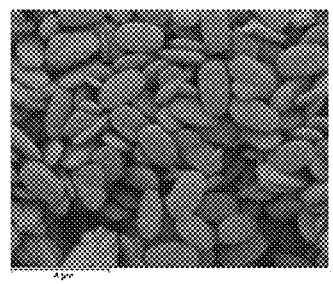
FIG. 16 shows a SEM micrograph of a product produced according to Example 3-2 and an indicated scale of 4 µm.
Figure 17:
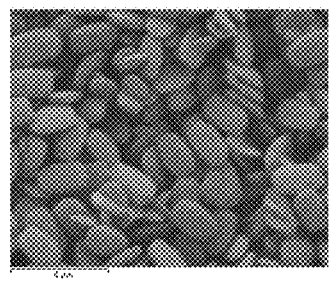
FIG. 17 shows a SEM micrograph of a product produced according to Example 3-3 and an indicated scale of 4 μm.
Figure 18:
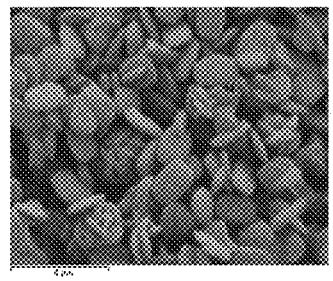
FIG. 18 shows a SEM micrograph of a product produced according to Example 3-4 and an indicated scale of 4 μm.
Figure 19:
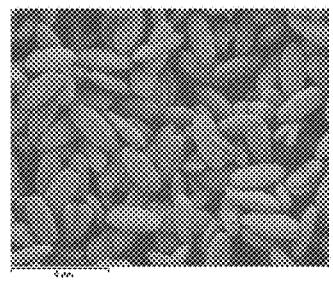
FIG. 19 shows a SEM micrograph of a product produced according to Example 3-5 and an indicated scale of 4 μm.
Figure 20:
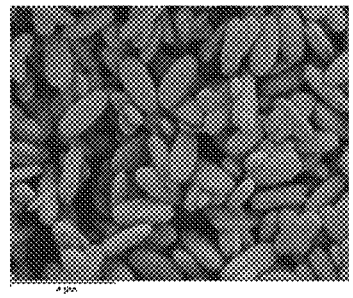
FIG. 20 shows a SEM micrograph of a product produced according to Example 3-6 and an indicated scale of 4 μm.
Figure 21:
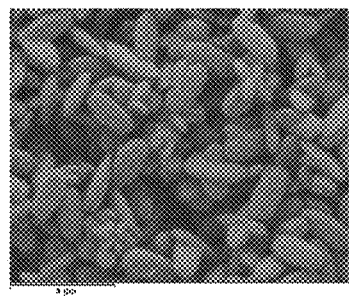
FIG. 21 shows a SEM micrograph of a product produced according to Example 3-7 and an indicated scale of 4 μm.
Figure 22:
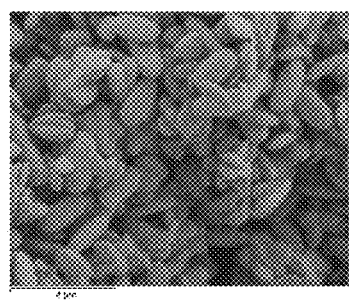
FIG. 22 shows a SEM micrograph of a product produced according to Example 3-8 and an indicated scale of 4 μm.
Figure 23:
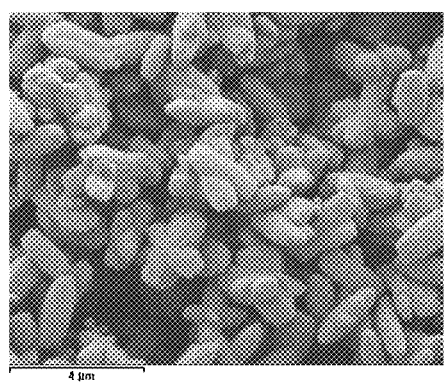
FIG. 23 shows a SEM micrograph of a product produced according to Example 4-1 and an indicated scale of 4 μm.
Figure 24:
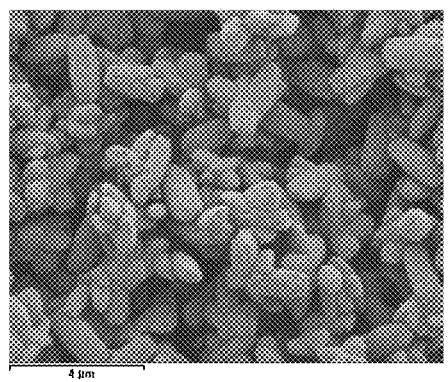
FIG. 24 shows a SEM micrograph of a product produced according to Example 4-2 and an indicated scale of 4 μm.
Figure 25:
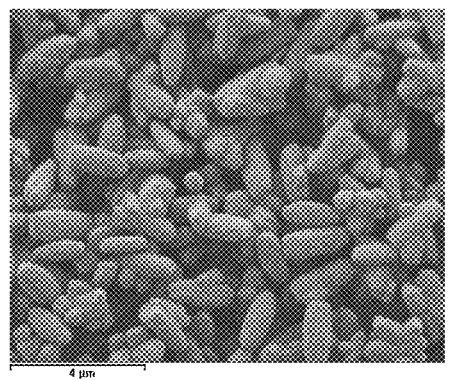
FIG. 25 shows a SEM micrograph of a product produced according to Example 4-3 and an indicated scale of 4 μm.
Figure 26:
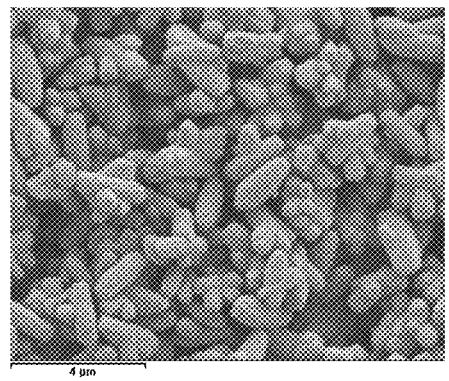
FIG. 26 shows a SEM micrograph of a product produced according to Example 4-4 and an indicated scale of 4 μm.

FIG. 1 is an SEM micrograph of the crystals produced in accordance with Example 1, having a 548 m$^2$/g total BET surface area, and a 104 m$^2$/g external surface area. FIG. 2 is an XRD pattern, recorded on a STOE Stadi-P Combi transmission XRD with CuKα radiation, of the crystals of FIG. 1.

Example 2: Control of Crystal Size of EUO Using Colloidal EUO Seeds

Raw Materials:
Alumina source: Aluminum sulphate solution made from Al$_2$(SO$_4$)$_3$.18H$_2$O as supplied by Aldrich.
Silica source: Ludox AS40 as supplied by Sigma-Aldrich.
Alkali source: KOH solution made from KOH pellets as supplied by Baker (85% purity).
Template (R): N,N,N,N',N',N'-hexamethylhexanediammonium bromide as supplied by Sigma-Aldrich (95%+ purity).
Seed slurry as prepared according to Example 1 outlined above with concentration of 0.906 weight % for Runs 1-16 and 0.091 weight % for Runs 17-32.
Molar composition of synthesis mixture: 0.011 Al$_2$O$_3$/0.2 KOH/0.2 Q/SiO$_2$/65 H$_2$O+ seeds Synthesis mixture preparation: Typically 144.7 parts of water were loaded into the synthesis reactor and 7.1 parts of the KOH solution was added under stirring. Subsequently, 3.5 parts of the alumina solution and 55.1 parts of the template (Q) were added to this mixture which was stirred until homogeneous before 11 parts of the seed solution and finally 28.5 parts of the silica source were added.

Crystallization conditions: The reactor was closed and heated to 160° C. with a heating rate of 20° C./hour under static conditions. After 168 hours of crystallization, the reactor was cooled to room temperature, the solid separated from the liquid by centrifugation and washed several times with deionized water.

Characterization: All the products were pure ZSM-50 according to X-ray diffraction and the particle size as determined by laser sizing is expressed as the d$_{50}$ of the particles. The results are summarized in Table 1 below and FIGS. 3-14. The results clearly show that the particle size of EUO can be tuned while keeping the narrow particle size distribution by adjusting the seeding level. The particle size distribution is indicated by the span of the particles, which is the difference between d$_{90}$ and d$_{10}$ divided by d$_{50}$, with smaller numbers indicating narrower particle size distributions.

TABLE 1

| Run No. | Wt ppm EUO seeds | d$_{50}$ (μm) | Span (d$_{90}$ − d$_{10}$/d$_{50}$) |
|---|---|---|---|
| 2-1 | 400 | 1.4 | 1.5 |
| 2-2 | 400 | 1.3 | 1.3 |
| 2-3 | 200 | 1.5 | 1.1 |
| 2-4 | 200 | 1.5 | 1.1 |
| 2-5 | 150 | 1.6 | 1.1 |
| 2-6 | 150 | 1.6 | 1.1 |
| 2-7 | 100 | 1.8 | 1.2 |
| 2-8 | 100 | 1.8 | 1.1 |
| 2-9 | 75 | 1.9 | 1.1 |
| 2-10 | 75 | 2.0 | 1.2 |
| 2-11 | 50 | 2.2 | 1.2 |
| 2-12 | 50 | 2.2 | 1.3 |
| 2-13 | 25 | 2.8 | 1.4 |
| 2-14 | 25 | 2.8 | 1.4 |
| 2-15 | 25 | 3.0 | 1.5 |
| 2-15 | 25 | 2.9 | 1.5 |
| 2-17 | 25 | 4.2 | 1.6 |
| 2-18 | 25 | 4.1 | 1.6 |
| 2-19 | 25 | 4.3 | 1.6 |
| 2-20 | 25 | 4.2 | 1.6 |
| 2-21 | 10 | 6.1 | 1.4 |
| 2-22 | 10 | 6.1 | 1.4 |
| 2-23 | 10 | 6.1 | 1.4 |
| 2-24 | 10 | 6.2 | 1.4 |
| 2-25 | 5 | 8.2 | 1.4 |
| 2-26 | 5 | 8.3 | 1.4 |
| 2-27 | 5 | 7.9 | 1.4 |
| 2-28 | 5 | 8.1 | 1.4 |
| 2-29 | 1 | 10.7 | 1.3 |
| 2-30 | 1 | 11.3 | 1.3 |
| 2-31 | 1 | 11.3 | 1.3 |
| 2-32 | 1 | 11.2 | 1.3 |

Example 3: Control of Crystal Size of EUO Using Colloidal EUO Seeds

Raw Materials:
Alumina source: Aluminum sulphate solution made from Al$_2$(SO$_4$)$_3$.18H$_2$O as supplied by Aldrich.
Silica source: Ludox AS40 as supplied by Sigma-Aldrich.
Alkali source: KOH solution made from KOH pellets as supplied by Baker (85% purity).
Template (R): N,N,N,N',N',N'-hexamethylhexanediammonium bromide as supplied by Sigma-Aldrich (95%+ purity).
Seed slurry as prepared according to Example 1 outlined above with concentration of 0.906 weight %.
Molar composition of synthesis mixture: 0.011 Al$_2$O$_3$/x KOH/0.2 Q/SiO$_2$/y H$_2$O+400 wt ppm seeds on total weight of the synthesis mixture.

Synthesis mixture preparation: The preparation was the same as described in Example 2, with adapted amounts of KOH and water.

Crystallization conditions: The reactor was closed and heated to 160° C. with a heating rate of 20° C./hour under static conditions. After 168 hours of crystallization, the reactor was cooled to room temperature, the solid separated from the liquid by centrifugation and washed several times with deionized water.

Characterization: All the products were pure ZSM-50 according to X-ray diffraction and the particle size as determined by laser sizing is expressed as the d$_{50}$ of the particles. The results are summarized in Table 2 below and FIGS. 15-22. The results show the possibility to prepare EUO particles having a small average size, d$_{50}$, and a very narrow particle size distribution. The particle size distribution is indicated by the span of the particles, which is the difference between d$_{90}$ and d$_{10}$ divided by d$_{50}$, with smaller numbers indicating narrower particle size distributions.

TABLE 2

| Run No. | KOH/SiO$_2$ | H$_2$O/SiO$_2$ | d$_{50}$ (μm) | Span (d$_{90}$ − d$_{10}$/d$_{50}$) |
|---|---|---|---|---|
| 3-1 | 0.2 | 60 | 1.6 | 1.2 |
| 3-2 | 0.2 | 65 | 1.5 | 1.1 |
| 3-3 | 0.2 | 70 | 1.5 | 1.0 |
| 3-4 | 0.2 | 75 | 1.5 | 1.0 |
| 3-5 | 0.25 | 60 | 1.7 | 1.3 |
| 3-6 | 0.25 | 65 | 1.6 | 1.2 |
| 3-7 | 0.25 | 70 | 1.5 | 1.1 |
| 3-8 | 0.25 | 75 | 1.5 | 1.1 |

While various embodiments have been described, it is to be understood that variations and modifications may be resorted to as will be apparent to those skilled in the art. Such variations and modifications are to be considered within the purview and scope of the claims appended hereto.

Example 4: Control of Crystal Size of EUO Using Colloidal EUO Seeds

Raw Materials:
Alumina source: Aluminum sulphate solution made from Al$_2$(SO$_4$)$_3$.18H$_2$O as supplied by Aldrich.
Silica source: Ludox AS40 as supplied by Sigma-Aldrich.
Alkali source: NaOH solution made from NaOH pellets as supplied by Sigma (p.a. 99.998% purity).
Template (R): N,N,N,N',N',N'-hexamethylhexanediammonium bromide as supplied by Sigma-Aldrich (95%+ purity).
Seed slurry as prepared according to Example 1 outlined above with concentration of 0.906 weight %.
Molar composition of synthesis mixture: 0.011 Al$_2$O$_3$/0.29 NaOH/0.2 Q/SiO$_2$/y H$_2$O+400 wt ppm seeds on total weight of the synthesis mixture.
Synthesis mixture preparation: The preparation was the same as described in Example 2, with adapted amounts of water.
Crystallization conditions: The reactor was closed and heated to 160° C. with a heating rate of 20° C./hour under static conditions. After 168 hours of crystallization, the reactor was cooled to room temperature, the solid separated from the liquid by centrifugation and washed several times with deionized water.
Characterization: All the products were pure ZSM-50 according to X-ray diffraction and the particle size as determined by laser sizing is expressed as the d$_{50}$ of the particles. The results are summarized in Table 3 below and FIGS. 23-26. The results show the possibility to prepare EUO particles having a tailored average size, d$_{50}$, and a tailored particle size distribution. The particle size distribution is indicated by the span of the particles, which is the difference between d$_{90}$ and d$_{10}$ divided by d$_{50}$, with smaller numbers indicating narrower particle size distributions.

TABLE 3

| Run No. | NaOH/SiO$_2$ | H$_2$O/SiO$_2$ | d$_{50}$ (μm) | Span (d$_{90}$ − d$_{10}$/d$_{50}$) |
|---|---|---|---|---|
| 4-1 | 0.29 | 60 | 3.7 | 2.9 |
| 4-2 | 0.29 | 65 | 2.9 | — |
| 4-3 | 0.29 | 70 | 2.0 | 2.0 |
| 4-4 | 0.29 | 75 | 1.7 | 1.3 |

Example 5: Comparative Example Using Powder EUO Seeds

Raw Materials:
Alumina source: Aluminum sulphate solution made from Al$_2$(SO$_4$)$_3$.18H$_2$O as supplied by Aldrich.
Silica source: Ludox AS40 as supplied by Sigma-Aldrich.
Alkali source: KOH solution made from KOH pellets as supplied by Baker (85% purity).
Template (R): N,N,N,N',N',N'-hexamethylhexanediammonium bromide as supplied by Sigma-Aldrich (95%+ purity).
EUO seed as prepared according to Example 1 outlined above and dried at 120° C. for 16 hr.
Molar composition of synthesis mixture: 0.011 Al$_2$O$_3$/0.2 KOH/0.2 Q/SiO$_2$/65 H$_2$O+x wt ppm seeds on total weight of the synthesis mixture
Synthesis mixture preparation: The preparation was the same as described in Example 2, with adapted amounts of seeds.
Crystallization conditions: The reactor was closed and heated to 160° C. with a heating rate of 20° C./hour under static conditions. After 168 hours of crystallization, the reactor was cooled to room temperature, the solid separated from the liquid by centrifugation and washed several times with deionized water.
Characterization: All the products were pure ZSM-50 according to X-ray diffraction and the particle size as determined by laser sizing is expressed as the d$_{50}$ of the particles. The results are summarized in Table 4 below. The results indicate that the dried powder seeds are much less effective seeds as a seeding level of up to 2000 ppm results in very large particles with a rather broad size distribution. The particle size distribution is indicated by the span of the particles, which is the difference between d$_{90}$ and d$_{10}$ divided by d$_{50}$, with smaller numbers indicating narrower particle size distributions.

TABLE 4

| Run No. | ppm Seeds | H$_2$O/SiO$_2$ | d$_{50}$ (μm) | Span (d$_{90}$ − d$_{10}$/d$_{50}$) |
|---|---|---|---|---|
| 5-1 | 1000 | 65 | 17 | 4.6 |
| 5-2 | 2000 | 65 | 17 | 4.5 |

The invention claimed is:
1. A process for the synthesis of a crystalline molecular sieve material having the EUO framework type, the process comprising:
   (a) providing a synthesis mixture suitable for the formation of an EUO framework type molecular sieve and comprising N,N,N,N',N',N'-hexamethylhexanediammonium, Q, cations and a colloidal suspension of seed crystals of an EUO framework type molecular sieve, wherein said seed crystals have an average diameter of 300 nanometers or less;
   (b) crystallizing said synthesis mixture; and
   (c) recovering from said synthesis mixture an EUO framework type molecular sieve in the form of individual crystals and/or aggregates of crystals having an average size, d$_{50}$, as measured by laser scattering, of less than 15 μm.
2. The process of claim 1, wherein said individual crystals and/or aggregates of crystals have an average size, d$_{50}$, as measured by laser scattering, of less than 5 μm.

3. The process of claim 1, wherein said individual crystals and/or aggregates of crystals have a span ($d_{90}-d_{10}/d_{50}$) of less than 2.0.

4. The process of claim 1, wherein the synthesis mixture contains from about 0.1 ppm to about 2,000 ppm by weight of said seed crystals of the EUO framework type, based on the total weight of the synthesis mixture.

5. The process of claim 1, wherein the synthesis mixture contains from 1 ppm to 500 ppm by weight of seed crystals of the EUO framework type, based on the total weight of the synthesis mixture.

6. The process of claim 1, wherein the synthesis mixture further comprises a source of an alkali or alkaline earth metal (M), a source of an oxide of a tetravalent element Y, a source of a trivalent element X, and water, and has a composition, in terms of mole ratios, within the following ranges:

$YO_2/X_2O_3$ at least 30;
$H_2O/YO_2$ about 15 to about 80;
$OH^-/YO_2$ about 0.2 to about 0.8;
$M/YO_2$ about 0.2 to about 0.8; and
$Q/YO_2$ about 0.05 to about 0.5.

7. The process of claim 1, wherein the crystallizing (b) is conducted at a temperature of 150 to 200° C.

8. A crystalline molecular sieve material having the EUO framework type produced by the process of claim 1.

9. A hydrocarbon conversion process comprising contacting a hydrocarbon feedstock under conversion conditions with an active form of the molecular sieve of claim 8.

10. A crystalline molecular sieve material having the EUO framework type and composed of individual crystals and/or aggregates of crystals having an average size, $d_{50}$ as measured by laser scattering, of 1 to less than 2 μm and a span ($d_{90}-d_{10}/d_{50}$) of 1.0 to 1.3.

11. A process for the synthesis of a crystalline molecular sieve having the EUO framework type by crystallization of a synthesis mixture suitable for the manufacture of that molecular sieve, the process comprising the step of adjusting the amount of colloidal seed crystals having an EUO framework type present in the synthesis mixture to control the particle size and/or span of the molecular sieve, wherein said amount of seeds is in a range of 0.1 ppm to 2,000 ppm by weight, based on the total weight of the synthesis mixture, wherein said colloidal seed crystals have an average diameter of 300 nanometers or less.

12. The process of claim 11, wherein said amount of seeds is in the range of 1 ppm to 500 ppm by weight, based on the total weight of the synthesis mixture.

* * * * *